US00PP37077P3

(12) United States Plant Patent
Boynton-Steele

(10) Patent No.: US PP37,077 P3
(45) Date of Patent: Oct. 28, 2025

(54) ***SALVIA* PLANT NAMED 'DH003'**

(50) Latin Name: *Salvia hybrida*
Varietal Denomination: DH003

(71) Applicant: Desert Honed LLC, Boise, ID (US)

(72) Inventor: Nicholas A. Boynton-Steele, Boise, ID (US)

(73) Assignee: Desert Honed LLC, Boise, ID (US)

( * ) Notice: Subject to any disclaimer, the term of this patent is extended or adjusted under 35 U.S.C. 154(b) by 0 days.

(21) Appl. No.: 19/037,225

(22) Filed: Jan. 26, 2025

(65) Prior Publication Data

US 2025/0248322 P1 Jul. 31, 2025

Related U.S. Application Data

(60) Provisional application No. 63/627,192, filed on Jan. 31, 2024.

(51) Int. Cl.
*A01H 5/02* (2018.01)
*A01H 6/50* (2018.01)

(52) U.S. Cl.
USPC ..... Plt./475
CPC ..... *A01H 6/508* (2018.05)

(58) Field of Classification Search
USPC ..... Plt./475
See application file for complete search history.

*Primary Examiner* — Susan McCormick Ewoldt
(74) *Attorney, Agent, or Firm* — Weatherly IP Solutions, LLC; James Weatherly; Karen P. Bechtold

(57) ABSTRACT

A new *Salvia* plant designated 'DH003' particularly distinguished by an evergreen shrub with a height of 100 cm and 4 to 6 glomerules per inflorescence, is disclosed.

1 Drawing Sheet

CROSS REFERENCE TO RELATED MATTER

The present application claims priority to U.S. Application No. 63/627,192, as filed on Jan. 31, 2024, the entire contents of which is incorporated herein by reference for all purposes.

Genus and species: *Salvia hybrida.*

Variety denomination: 'DH003'.

BACKGROUND OF THE NEW PLANT

The present invention comprises a new and distinct variety of *Salvia*, botanically known as *Salvia hybrida*, and hereinafter referred to by the variety name 'DH003'. 'DH003' originated from a cross of the proprietary female *Salvia* plant '1402-3-T1' (unpatented) and the proprietary male *Salvia* plant '1608-5-T1' (unpatented) in June 2019 in Boise, Idaho.

In fall of 2019 seeds were planted and a plant named 'DH003' was identified in the summer of 2020. 'DH003' was first vegetatively propagated by vegetative cuttings in Boise, Idaho. 'DH003' was found to reproduce true to type in successive generations of asexual propagation in Boise, Idaho via vegetative cuttings.

SUMMARY

The following are the most outstanding and distinguishing characteristics of 'DH003' when grown under normal horticultural practices in Boise, Idaho.

1. 4 to 6 glomerules per inflorescence;
2. Evergreen shrub; and
3. Shrub height of 100 cm.

DESCRIPTION OF THE PHOTOGRAPHS

These new *Salvia* plants are illustrated by the accompanying photographs of plants grown in a greenhouse in Boise, Idaho. The colors shown are as true as can be reasonably obtained by conventional photographic procedures.

DESCRIPTION OF 'DH003'

Figure 1:
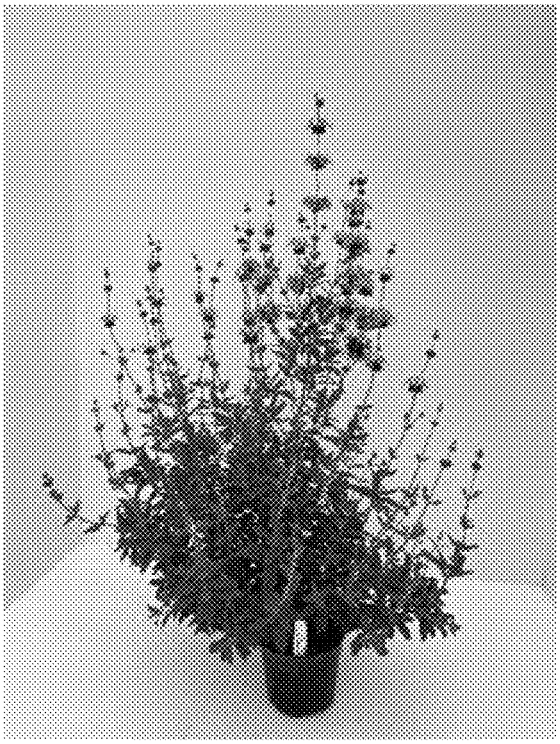
FIG. 1 is a whole plant photo of 'DH003' showing foliage, buds, and flowers. The photo is of a 2-year-old plant taken in March 2021 in Boise, Idaho.
Figure 2:
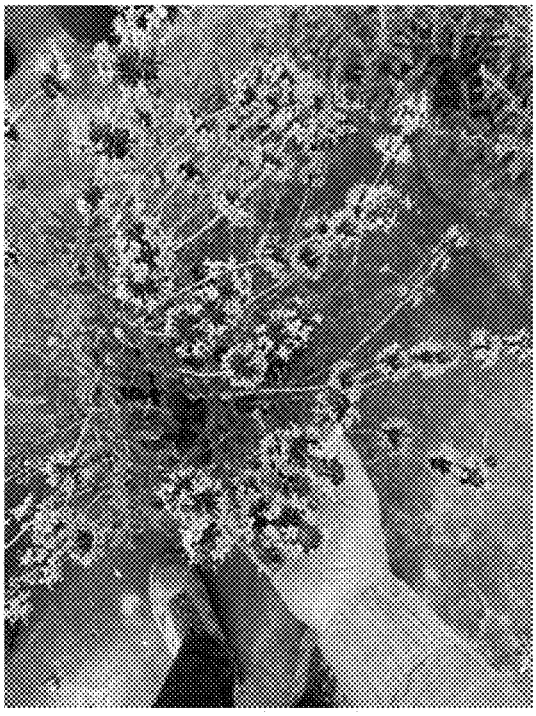
FIG. 2 is close-up photo of 'DH003' showing foliage, buds, and flowers. The photo is of a 3-year-old plant taken in June 2022 in Boise, Idaho.

The following detailed descriptions set forth the distinctive characteristics of 'DH003'. The data which define these characteristics were collected from asexual reproductions carried out in Boise, Idaho. Data was collected in January 2024 on 1 year old cuttings in 3 gallon containers grown in a plastic greenhouse. Color references are to The R.H.S. Colour Chart of The Royal Horticultural Society of London (R.H.S.), $4^{th}$ edition (2001).

Classification:

*Family.*—Lamiaceae.
*Genus.*—*Salvia.*
*Species.*—*Hybrida.*
*Common name.*—Sage.

Parents:

*Female parent.*—*Salvia* plant '1402-3-T1' (unpatented).
*Male.*—*Salvia* plant '1608-5-T1' (unpatented).

Plant:

*Propagation method.*—Cutting.
*Rooting system.*—Fibrous.
*Time to develop roots.*—2 to 3 weeks.
*Crop time.*—8 weeks for 1 gallon container, 12 to 14 weeks for a 3 to 5 gallon container.
*Suggested container size.*—One gallon or 3 to 5 gallon.

*Use*.—Home gardens, commercial landscapes, native gardens, waterwise gardens.
*Type*.—Perennial.
Overall dimensions.—100 cm tall x 130 cm wide.
*Cultural requirements*.—In ground, full to partial sun, infrequent deep watering, light shearing after main bloom season will keep the shrub compact.
*In containers*.—Full sun, well drained media, consistently moist, pinched in plug stage, pinched at least once more for a one gallon, at least twice more for a 3 or 5 gallon.
*Hardiness*.—Zone 8a.
*Form*.—Compact, rounded shrub.
*Growth habit*.—Compact.
*Blooming season*.—Spring through midsummer.
*Lastingness of blooms*.—Each flower lasts 2 days, each inflorescence lasts 4-6 weeks.

Stems (below first pinch):
*Condition*.—Semi-ripe wood.
*Bark*.—Greyed Brown 199B.
*Shape*.—Square in cross section.
*Length*.—11.0 cm.
*Diameter*.—0.3 cm.
*Stem color* (*where exposed beneath bark*).—RHS 193A.
*Shape*.—Square becoming round with age.
*Texture*.—Smooth slightly tomentose becoming rougher with age.

Branches:
*Quantity*.—Too many to count.
*Shape*.—Square in cross section.
*Length*.—11 cm to 20 cm.
*Width*.—0.3 cm.
*Internode length*.—0.8 cm to 1.9 cm.
*Color*.—RHS 193A.
*Anthocyanin*.—Absent.

Leaves:
*Type, arrangement*.—Opposite.
*Attachment*.—Petiolate.
*Quantity per branch*.—At least 18.
*Shape*.—Ovate to elliptic.
*Length* (*mature*).—2.9 cm to 4.4 cm.
*Width* (*mature*).—1.6 cm to 2.1 cm.
*Margin*.—Crenate.
*Thickness*.—0.5 cm.
*Surface* (*adaxial*).—Rugose, slightly glandular pubescent.
*Surface* (*abaxial*).—Net-veined, glandular pubescent.
*Color* (*adaxial surface*).—RHS 189A.
*Color* (*abaxial surface*).—RHS 191B.
*Venation*.—Pinnate in pattern, recessed from upper surface, protruding from lower surface.
*Vein color*.—RHS 191D.
*Apex*.—Rounded.
*Base*.—Rounded to cuneate.
*Fragrance*.—Musk, camphor, cineole.
*Stipules*.—Absent.

Petiole:
*Shape*.—"D" shaped in cross section.
*Length*.—0.6 cm to 1.2 cm.
*Width*.—0.15 cm.
*Texture*.—Slightly tomentose.
*Color*.—RHS 191D.

Peduncle:
*Length* (*from uppermost leaf pair to base of lowest whorl of flowers*).—approximately 8.7 cm to 9.2 cm.
*Shape*.—Square in cross section.
*Width*.—0.25 cm.
*Texture*.—Slightly tomentose.
*Color*.—Base color of RHS 145B with overtones of RHS N79B.

Inflorescence:
*Type*.—Paniculate verticillaster, typically 4 glomerules per stem.
*Flower arrangement*.—Opposite cyme.
*Length*.—22 cm to 26 cm.
*Width*.—5 cm to 7 cm.
*Number of florets per node*.—Approximately 8 to 28.

Bracts:
*Size*.—Lower bracts: Length: 0.9 cm. Width: 0.7 cm. Upper bracts: Length: 0.6 cm. Width: 0.3 cm.
*Shape*.—Ovate to elliptic.
*Color*.—RHS N79A at the apex fading to RHS 142C toward the base.

Calyx:
*Shape*.—Tube.
*Length*.—1.0 cm.
*Width at base*.—0.1 cm.
*Width across sepal apices*.—0.4 cm.

Sepals: Fused into calyx tube with 3 lobes, 1 adaxial, 2 abaxial.
*Length*.—0.03 cm (abaxial) and 0.05 cm (adaxial) from where tube flares into lobes to the apex.
*Width*.—0.01 cm (abaxial) and 0.03 cm (adaxial).
*Shape*.—Fused into tube, calyx lobes tapering to an acute apex.
*Apex*.—Acute.
*Base*.—Fused to calyx tube.
*Margin*.—Entire.
*Texture*.—Interior: Smooth. Exterior: Slightly tomentose.
*Color* (*both surfaces*).—RHS N79A at the apex fading to RHS 142C toward the base.

Flowers:
*Quantity*.—30 (or more) per glomerule.
*Aspect*.—45 degrees in relation to peduncle.
*Shape*.—Tubular, opening to a bi-radially symmetric flower.
*Blooming period*.—Early to late summer.
*Persistence*.—Individual flowers last two days, individual inflorescences last 4-6 weeks.
*Fragrance*.—None.

Bud:
*Shape*.—Tube shaped with a rounded end.
*Dimensions* (*immediately before petal emergence*).—Length: 0.9 cm to 1.0 cm. Diameter: 0.3 cm.
*Color*.—RHS 90C.
*Surface*.—Smooth.

Corolla:
*Shape*.—Tubular, opening to a bi-radially symmetric flower with 5 petals.
*Length*.—1.9 cm to 2.1 cm.
*Width*.—Widest point of tube 0.4 cm; upper petal is 1.3 cm; lower petal is 1.5 cm.
*Texture* (*both surfaces*).—Smooth.
*Color* (*both surfaces*).—RHS 92C fading to RHS 84D at the base of the tube.

Petals:

*Quantity.*—5.

*Arrangement.*—Tubular, opening to a bi-radially symmetric flower with 5 lobes.

*Upper petal.*—Shape: Elliptic. Length: 0.06 cm. Width: 0.3 cm. Texture: Adaxial surface: Smooth. Abaxial surface: Smooth. Apex: Rounded. Base: Fused to corolla tube. Margin: Entire. Color (both surfaces): RHS 92C.

*Lower petal, lip.*—Shape: Two lobed, elongated with elliptic lobes. Length: 0.5 cm, each lobe 0.2 cm long. Width: 0.03 cm to 0.04 cm. Texture (both surfaces): Smooth. Apex: Rounded. Base: Fused to corolla tube. Color (both surfaces): RHS 92C.

*Lower petal, lateral lobes.*—Shape: Elliptic. Length (each lateral lobe): 0.03 cm. Width: 0.02 cm. Texture: Adaxial surface: Smooth. Abaxial surface: Smooth. Apex: Rounded. Base: Fused to corolla tube. Margin: Entire. Color (both surfaces): RHS 92C.

Reproductive organs:

*Stamens.*—Quantity: 2. Filaments: Length: 0.07 cm from anther to attachment with corolla tube. Color: RHS N88C on the upper part, RHS N92D on the lower part.

*Anthers.*—Attachment, shape: Basifixed. Length: 0.2 cm. Width: 0.05 cm. Color: RHS 93A.

*Pollen.*—Amount: Medium. Color: RHS 2B.

*Pistil.*—Quantity: 1. Style: Length: 2.5 cm. Diameter: 0.3 cm. Color: RHS 91B fading to RHS 91C at base.

*Stigma.*—Shape: Forked. Length: 0.5 cm to 1.0 cm. Diameter: 0.01 cm to 0.02 cm. Color: RHS 90A.

*Ovary.*—Shape: Cylindrical. Length: 0.1 cm. Diameter: 0.1 cm. Color: RHS 145C.

Seeds:

*Quantity.*—2.

*Shape.*—Flattened oval.

*Length.*—0.3 cm.

*Diameter.*—0.15 cm.

*Surface.*—Smooth, shiny.

*Color.*—RHS N199C with darker vein-like markings of RHS N199B.

Disease and pest susceptibility: Occasional Powdery Mildew. Occasional Pithium or other water mold susceptibility in water-logged or poorly drained soil. Occasional aphid infestation in early spring on new growth.

COMPARISON OF 'DH003' WITH PARENTAL LINES AND KNOWN VARIETY

'DH003' is distinguished from the female parent as described in Table 1 and the male patent as described in Table 2.

TABLE 1

Comparison with Female Parental Line

| Trait | Variety 'DH003' | Female parent '1402-3-T1' |
|---|---|---|
| Foliage retention | Evergreen | deciduous |

TABLE 2

Comparison with Male Parental Line

| Trait | Variety 'DH003' | Male Parent '1608-5-T1' |
|---|---|---|
| Glomerules per inflorescence | 4 to 6 | 1 to 2 |

'DH003' can be compared to the commercial *Salvia* variety 'Allen Chickering' (unpatented). Differences between the varieties are described in Table 3.

TABLE 3

Comparison with Similar Variety

| Trait | Variety 'DH003' | Commercial line 'Allen Chickering' |
|---|---|---|
| Height | 100 cm | 130 cm to160 cm |

I claim:

1. A new and distinct variety of *Salvia* plant named 'DH003' as shown and described herein.

* * * * *